US00PP32904P2

(12) United States Plant Patent
Olesen

(10) Patent No.: US PP32,904 P2
(45) Date of Patent: Mar. 23, 2021

(54) ROSE PLANT NAMED 'POULTC024'

(50) Latin Name: *Rosa hybrid*
Varietal Denomination: Poultc024

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,245

(22) Filed: Sep. 4, 2019

(51) Int. Cl.
*A01H 5/02* (2018.01)
*A01H 6/74* (2018.01)

(52) U.S. Cl.
USPC ..... Plt./108
CPC ..... *A01H 6/749* (2018.05)

(58) Field of Classification Search
USPC ..... Plt./108
CPC ..... A01H 5/0222
See application file for complete search history.

(56) References Cited

PUBLICATIONS http://www.poulsenroser.com/assortment/rose-collections/towne-country/red-easy.aspx; Aug. 1, 2020; 1 page.*

* cited by examiner

*Primary Examiner* — Kent L Bell

(57) ABSTRACT

A new garden rose plant of the ground cover class which has abundant, red flowers and attractive foliage. This new and distinct variety has shown to be uniform and stable in the resulting generations from asexual propagation.

3 Drawing Sheets

Botanical designation: *Rosa* hybrid.
Variety denomination: 'Poultc024'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poultc024', originated as a single seedling from the stated cross.

The new variety may be distinguished from its male pollen parent and female seed parent primarily by the following characteristics. The male pollen parent plant has single petal red flowers while the new variety has semi double red flowers. The female seed parent plant has orange flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance; and
4. Extended period of bloom.

This combination of qualities is not present in previously available commercial cultivars of this type, known to the inventor, and distinguish 'Poultc024' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poultc024' was selected in the spring of 2011 by the inventor as a single plant from the progeny of the aforementioned hybridization.

Asexual reproduction of 'Poultc024' by rooted cuttings was first done by Mogens N. Olesen in the nursery in Fredensborg, Denmark in July, 2011. This initial and other subsequent asexual propagations conducted in controlled environments have demonstrated that the characteristics of 'Poultc024' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc024'.

Specifically illustrated in FIG. 1 of the drawings are juvenile and mature leaves and stems.

Figure 1:
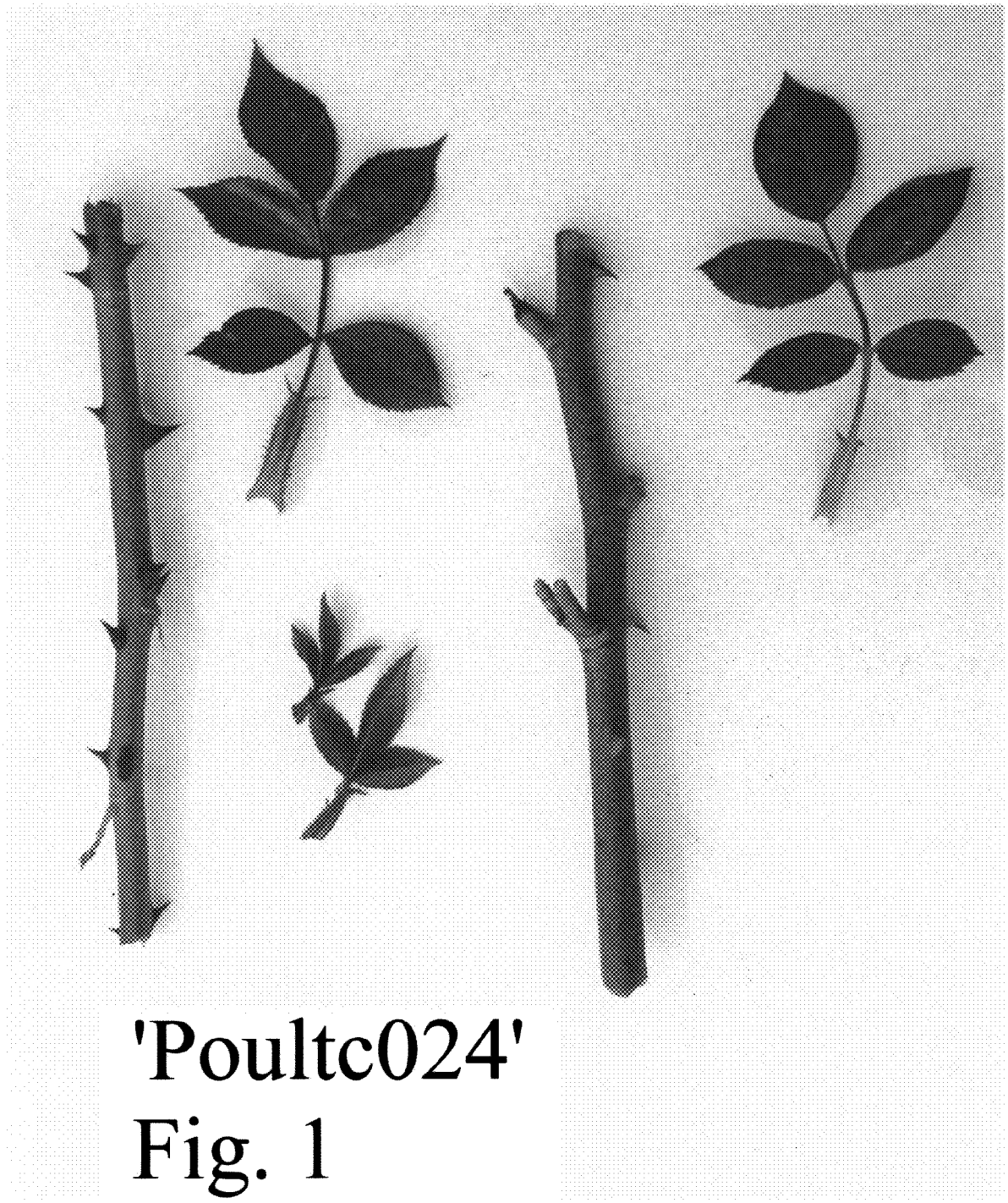
Figure 2:
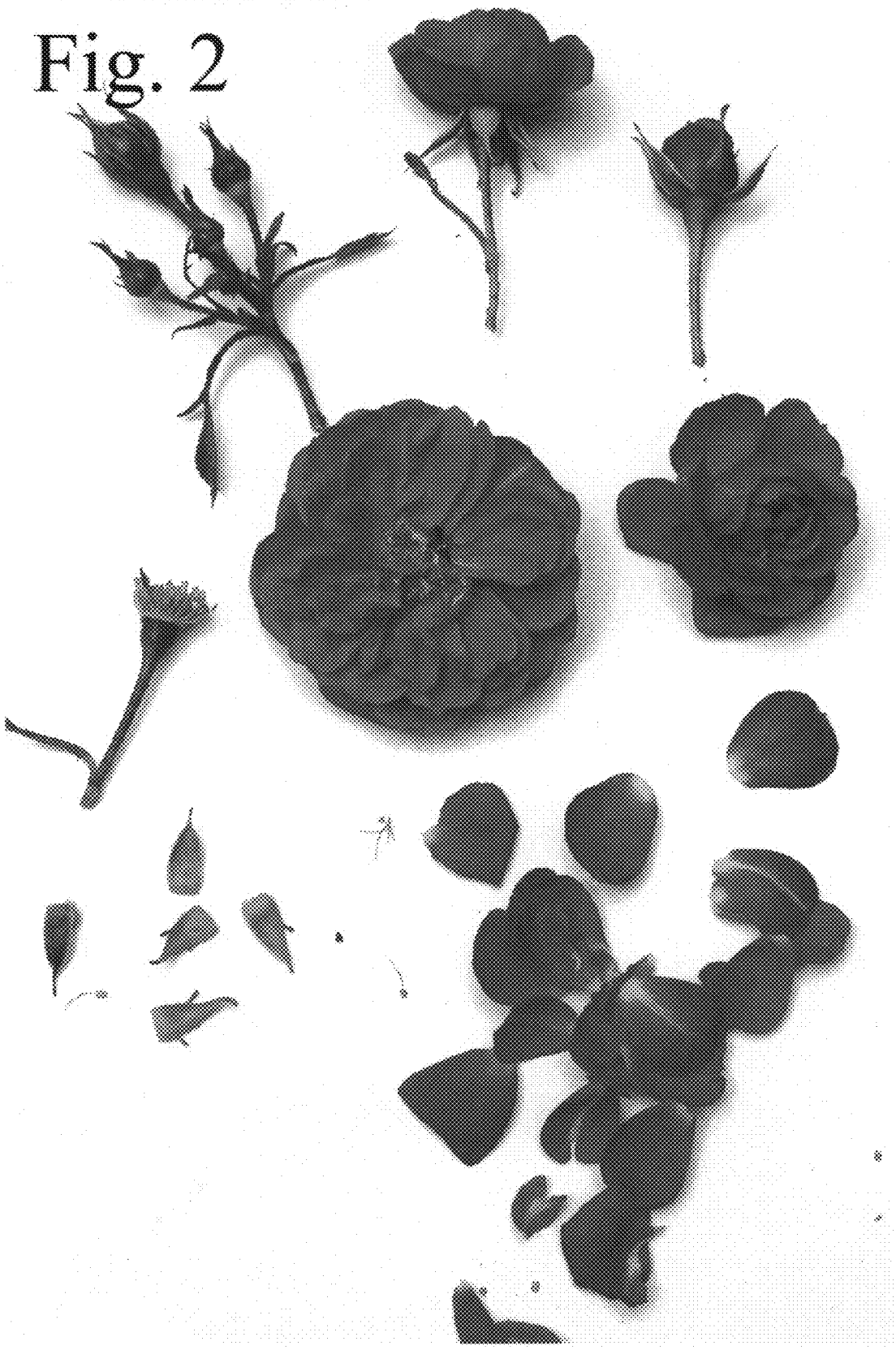

Specifically illustrated in FIG. 2 of the drawings are open flowers and reproductive flower parts, and flower buds.

Figure 3:
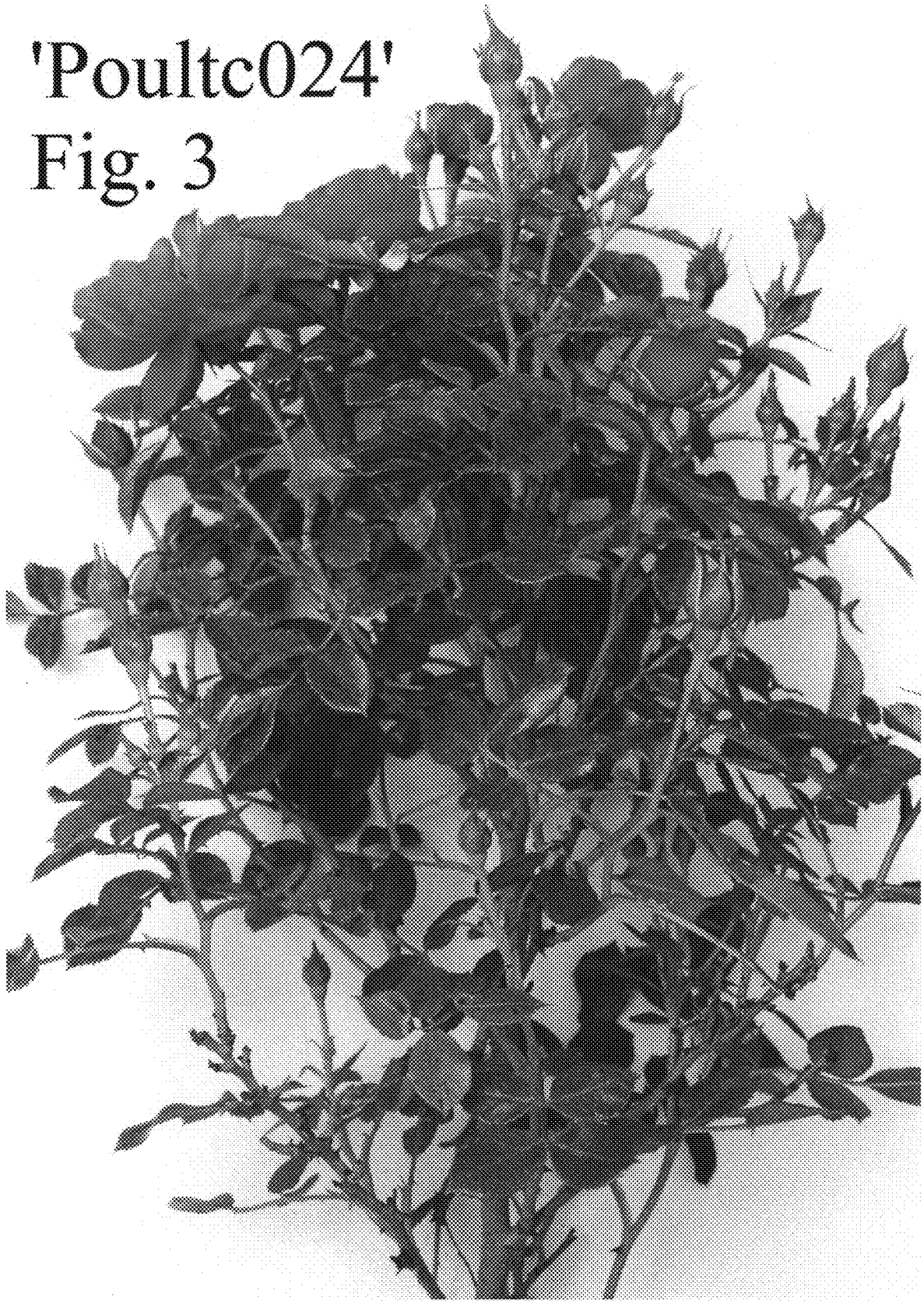

FIG. 3 shows a flowering branch. Plants shown are 2 years of age.

DETAILED DESCRIPTION OF THE VARIETY

The following is a description of 'Poultc024', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poultc018', U.S. Plant Pat. No. 26,533 are compared to 'Poultc024' in Chart 1.

CHART 1

| | 'Poultc024' | 'Poultc018' |
|---|---|---|
| Petal Count | 65 petals | 20 petals |
| Flower Diameter | 55 mm | 50 mm |
| General Tonality of Flower Color | Red Group 45B | Red Group 46A |

FLOWER AND FLOWER BUD

Blooming habit: Continuous.

Flower bud:

*Size*.—Upon opening, 15 mm in length from base of receptacle to end of bud. Bud diameter is 10 mm.

*Bud form*.—Ovoid.

*Bud color*.—As sepals divide petals are Red Group 53A.

*Sepal inner surface*.—Color: Yellow-Green Group 146D. Surface: Lightly pubescent.

*Sepal outer surface*.—Color: Yellow-Green Group 144A with intonations of Greyed-Red Group 182A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—15 mm long, 6 mm wide.

*Receptacle*.—Texture: Smooth. Size: 6 mm in height,6 mm wide. Color: Yellow-Green Group 144A with Greyed-Red Group 182A. Shape: Campanulate.

*Pedicel*.—Surface: Smooth. Length: 22 mm. Diameter: 2 mm on average. Color: Yellow-Green Group 144A. Strength: Strong.

*Peduncle*.—Length: 4 to 15 cm. Diameter: About 2.5 mm. Color: Yellow-Green Group 144B with intonations of Greyed-Red Group 182A. Texture: Rough with stipitate glands.

Flower bud development: Flower buds are borne in clusters of 5 to 7 flower buds per stem.

Flower bloom:

*Fragrance*.—Moderate.

*Duration*.—The blooms have a duration on the plant of approximately 10 days. Petals fall cleanly away from plant after flowers have fully matured.

*Size*.—Flower diameter is 55 mm when open. Flower depth is 27 mm.

*Flower shape*.—Rosette, semi double flower which opens up almost flat.

*Shape of flower, side view*.—The upper portion is flat convex. The lower portion is flat concave.

Petalage: Under normal conditions, flowers have about 65 petals.

General tonality of flower: Open flowers are Red Group 45B.

Petal color:

*Outer petals*.—Upper surface: Red Group 45B. Lower surface: Red Group 53A.

*Inner petals*.—Upper surface: Red Group 45B. Lower surface: Red Group 53A.

*Basal petal spots*.—Upper surface: Yellow Group 8D. Lower surface: Yellow Group 8D.

Petals:

*Petal reflex*.—Not reflexed.

*Margin*.—Entire and uniform.

*Shape*.—Elliptic. Apex shape: Rounded. Base shape: Acute.

*Size*.—18 mm (l)×17 mm (w).

*Texture*.—Smooth.

*Thickness*.—Average.

Petaloids:

*Size*.—10 mm (l) by 4 mm (w).

*Quantity*.—About 5.

*Shape*.—Elliptical with an acute base and rounded apices.

*Margin*.—Cleft at center.

*Color*.—Red Group 45B on the upper surface. The lower surface is Red Group 53A.

Reproductive flower parts:

*Pollen*.—None observed.

*Anthers*.—Size: 2 mm in length. Color: Yellow-Orange Group 18A. Quantity: 35 on average.

*Filaments*.—Color: Orange-Red Group 30D. Length: 5 mm.

*Pistils*.—Length: 3 mm. Quantity: 16 on average.

*Stigmas*.—Color: Greyed White 156D.

*Styles*.—Color: Red Group 53C

*Location of stigmas*.—Level in location relative to the length of the filaments and the height of the anthers.

*Hips*.—None Observed.

PLANT

Plant growth: Upright, bushy. Plants are 80 cm in height, and 80 cm wide.

Stems:

*Color of juvenile growth*.—Yellow-Green Group 144A.

*Color of mature growth*.—Yellow-Green Group 146C.

*Length*.—Canes are about 25 cm from the base of the plant to the flowering portion.

*Diameter*.—About 8 mm.

*Internodes*.—On mature canes about 10 mm between nodes.

*Surface texture*.—Young wood: Smooth. Older wood: Smooth.

Long prickles:

*Incidence:*.—10 prickles per 10 cm of stem.

*Size*.—Average length of prickles on mature stems is 7 mm.

*Shape*.—Upper portion is linear. Lower portion is concave.

*Color*.—Juvenile prickles: Greyed-Purple Group 184A. Mature prickles: Greyed-Orange Group 177B.

Plant foliage:

*Compound leaf*.—About 105 mm (l)×55 (w).

*Quantity*.—3 leaves per 10 cm of stem on average.

*Leaf bearing angle to the stem*.—45 degrees.

*Color of juvenile foliage*.—Upper side: Yellow-Green Group 144A with strong intonations of Greyed-Red Group 178A. Lower side: Yellow-Green Group 144A with strong intonations of Greyed-Red Group 178A.

*Color of mature foliage*.—Upper side: Yellow-Green Group 146A. Lower side: Yellow-Green Group 146B.

Plant leaves and leaflets:

*Stipules*.—Size: 20 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 2 mm. Upper surface color: Yellow-Green Group 144A. Lower surface color: Yellow-Green Group 144A.

*Rachis*.—Length: 45 mm. Diameter: 2 to 3 mm. Upper surface color: Yellow-Green Group 144A with intonations of Greyed-Red Group 181C. Lower surface color: Yellow-Green Group 144A.

*Leaflet*.—Quantity: Normally 5 to 7 leaflets. Margins: Serrated. Size: Terminal leaflets are about 34 mm long, 16 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Pest resistance: Average susceptibility to any pest normally associated with the species.

Heat tolerance: The variety has been found to be suitable for climate conditions found in the American Horticulture Society heat zone 7.

I claim:

1. A new and distinct variety of rose plant of the ground cover rose class named 'Poultc024', substantially as illustrated and described herein, due to its abundant red flowers, disease resistance, and extended period of bloom.

* * * * *

'Poultc024'

'Poultc024'

'Poultc024'